(12) United States Patent
Tortelli et al.

(10) Patent No.: US 8,742,142 B2
(45) Date of Patent: *Jun. 3, 2014

(54) PROCESS FOR PRODUCING PERFLUORINATED ORGANIC COMPOUNDS

(75) Inventors: Vito Tortelli, Milan (IT); Marco Galimberti, Milan (IT); Guiseppe Marchionni, Milan (IT)

(73) Assignee: Solvay Specialty Polymers Italy S.p.A., Bollate MI (IT)

( * ) Notice: Subject to any disclaimer, the term of this patent is extended or adjusted under 35 U.S.C. 154(b) by 155 days.

This patent is subject to a terminal disclaimer.

(21) Appl. No.: 13/378,887

(22) PCT Filed: Jul. 6, 2010

(86) PCT No.: PCT/EP2010/004081
§ 371 (c)(1),
(2), (4) Date: Dec. 16, 2011

(87) PCT Pub. No.: WO2011/003575
PCT Pub. Date: Jan. 13, 2011

(65) Prior Publication Data
US 2012/0095243 A1    Apr. 19, 2012

(30) Foreign Application Priority Data
Jul. 6, 2009  (EP) .................................... 09164697

(51) Int. Cl.
C07D 317/42  (2006.01)
(52) U.S. Cl.
USPC ........................................................ 549/449
(58) Field of Classification Search
None
See application file for complete search history.

(56) References Cited

U.S. PATENT DOCUMENTS

| | | | |
|---|---|---|---|
| 3,900,372 A | 8/1975 | Childs et al. | |
| 5,382,704 A | 1/1995 | Krespan et al. | |
| 5,466,877 A | 11/1995 | Moore | |
| 6,858,751 B1 | 2/2005 | Senet et al. | |
| 7,019,177 B2 * | 3/2006 | Tortelli et al. | 568/615 |
| 7,053,237 B2 | 5/2006 | Okazoe et al. | |
| 2007/0287855 A1 | 12/2007 | Geller et al. | |
| 2011/0160415 A1 * | 6/2011 | Marchionni et al. | 526/204 |

FOREIGN PATENT DOCUMENTS

| | | |
|---|---|---|
| EP | 1164122 A1 | 12/2001 |
| EP | 1621559 A2 | 2/2006 |
| GB | 1216639 A | 12/1970 |
| GB | 1226566 A | 3/1971 |
| WO | WO 0059859 A1 | 10/2000 |

OTHER PUBLICATIONS

Flosser, David A., et al—"A useful conversion of alcohols to alkyl fluorides", Tetrahedron Letters, 2002, vol. 43, No. 23, pp. 4275-4279, Elsevier Science Ltd; 5 pgs.

Olah, George A., et al—"Synthesis and Investigation of Organic Fluorine Compounds. XXV. The Preparation of Alkyl Fluoroformates and Remarks Relative to a New Published Preparation of Alkyl Fluorides", 1956, Journal of Organic Chemistry, vol. 21, No. 11, pp. 1319-1320, American Chemical Society; 2 pgs.

Conte, Lino, et al—"Electrochemical fluorination: state of the art and future tendences", 2004, Journal of Fluorine Chemistry, vol. 125, No. 2, pp. 139-144, Elsevier B.V.; 6 pgs.

* cited by examiner

Primary Examiner — Sun Jae Yoo

(57) ABSTRACT

A process for producing a perfluorinated functional compound is disclosed, which comprises:

A. converting an at least partially hydrogenated alcohol into an at least partially hydrogenated fluoroformate compound;

B. reacting said at least partially hydrogenated fluoroformate compound with fluorine in the presence of at least one (per)haloolefin comprising at least one carbon-carbon double bond and having at least one fluorine or chlorine atom on either one of the carbon atoms of said double bond, to obtain a perfluorinated fluoroformate compound.

11 Claims, No Drawings

PROCESS FOR PRODUCING PERFLUORINATED ORGANIC COMPOUNDS

TECHNICAL FIELD

Cross-Reference to Related Applications

This application is a U.S. national stage entry under 35 U.S.C. §371 of International Application No. PCT/EP2010/004081 filed Jul. 6, 2010, which claims priority to European application No. 09164697.6 filed on Jul. 6, 2009, the whole content of which being incorporated herein by reference for all purposes.

The invention relates to a process for producing functionalized perfluorinated organic compounds from hydrogen-containing alcohols.

BACKGROUND ART

It is known that perfluorinated organic compounds having functional moieties are useful intermediates for manufacturing a variety of valuable chemical compounds, such as notably perfluoromonomers (e.g. perfluorovinylethers) and fluorosurfactants.

A convenient approach for the synthesis of functional perfluorinated compounds involves fluorination of hydrogen-containing alcohols, the hydroxyl moiety being possibly derivatized to yield the target functional moiety. However, hydrocarbons containing functional hydroxyl moieties are generally unstable under conditions of traditional fluorination processes, typically comprising a first step carried out at low temperature and high dilution, followed by a further step involving high temperatures and concentrations of fluorine, as required in order to reach satisfactory yields of the perfluorinated compound. Under these conditions, it is generally understood that compounds having hydroxyl groups decompose, with simultaneous release of HF and $COF_2$, and subsequent formation of corresponding non-functional perfluorocompound having one less carbon atom than the starting hydroxyl-containing compound.

In order to overcome this problem, EP 1164122 A (ASAHI GLASS CO LTD) Dec. 19, 2001 discloses a process for producing fluorinated compounds wherein a primary hydrogenated alcohol is first converted into the corresponding ester, generally a partially fluorinated ester, as obtained by reaction with a (per)fluorinated acyl fluoride, and then subjected to fluorination in liquid phase. The so-obtained perfluorinated ester can be then thermally cleaved or decomposed with suitable agents, to obtain perfluorinated acyl fluoride corresponding to the starting hydrogenated alcohol.

Similarly, U.S. Pat. No. 7,053,237 (ASAHI GLASS CO LTD) Nov. 24, 2005 discloses a process for producing a fluorinated ester, wherein a primary hydrogenated alcohol is protected via transesterification and then subjected to fluorination in liquid phase.

However, the above described processes have the drawback that, in order to prevent decomposition of the reagents due to the reaction exothermicity, it may be necessary to operate under diluted concentrations both of fluorine and of the hydrogen-containing alcohol. Furthermore, to obtain a fully fluorinated product, a large excess of fluorine over the stoichiometrically required quantity, is needed. These conditions might negatively affect the reaction rate, yielding low productivity of the overall process.

Furthermore, as already mentioned, in order to reduce fluorine consumption, protection of the alcohol moiety as an ester is generally performed using suitable perfluorinated carboxylic acid derivatives, generally acyl fluorides, whose availability might be costly and induce further steps for appropriate separation, recovery and reuse.

As an alternative to this pathway, hydrogen-containing alcohols have been protected under the form of fluoroformates before undergoing fluorination.

Thus, U.S. Pat. No. 3,900,372 (PHILLIPS PETROLEUM) Aug. 19, 1975 discloses a process for the production of perfluorinated organic compounds from hydrogen-containing alcohols. The process comprises protection of the hydroxyl moieties of the hydrogen-containing alcohol by reaction with carbonyl fluoride to yield corresponding hydrogen-containing fluoroformates. Said fluoroformates are then subjected to an electrochemical fluorination step, and the resulting perfluorinated counterparts still possessing the fluoroformate functionality are subsequently cleaved by the action of fluoride ions under reacting conditions for yielding corresponding acyl fluorides. Further, it is known that perfluorinated fluoroformates can be converted into fluoroacyl fluorides with loss of carbonyl fluoride, easy to separate and recover.

Nevertheless, electrochemical fluorination is a burdensome and energy-consuming procedure, which is generally less economically and industrially acceptable than fluorination with elemental fluorine, particularly when a single compound has to be obtained. Furthermore, yields in electrochemical fluorination are known to be mostly moderate or even poor, especially if high molecular weight compounds have to be fluorinated.

Attempts to fluorinate with molecular fluorine certain fluoroformates have been already disclosed in the art. In particular, GB 1226566 (MONTECATINI EDISON) Mar. 31, 1971 discloses a process for the preparation of certain perfluorinated polyethers wherein possible terminal groups of acidic nature, such as formate moiety, are eliminated. Conversion by severe heat treatment of a perfluorinated polyether having a fluoroformate terminal group into a fluoroacyl fluoride is also described.

There is thus still a need in the art for a process for producing perfluorinated compounds having a functional moiety from hydrogen-containing alcohols comprising a fluorination step that may be carried out under mild conditions and providing high yields.

DISCLOSURE OF INVENTION

It is thus an object of the present invention to provide a process for producing a perfluorinated compound comprising functional moieties from relatively inexpensive hydrogen-containing alcohols, which does not involve the use of expensive perfluorocarboxylic derivatives nor of burdensome electrochemical fluorination, which advantageously evolves with high yields.

The process of the invention thus comprises:
A. converting an at least partially hydrogenated alcohol into corresponding at least partially hydrogenated fluoroformate compound;
B. reacting said at least partially hydrogenated fluoroformate compound with fluorine in the presence of at least one (per) haloolefin comprising at least one carbon-carbon double bond and having at least one fluorine or chlorine atom on either one of the carbon atoms of said double bond, to obtain a perfluorinated fluoroformate compound.

In the present specification and in the claims the expression "at least partially hydrogenated" when referred to an alcohol or a fluoroformate is meant to indicate that said alcohol or said fluoroformate contains at least one C—H bond.

The presence of a (per)haloolefin in step B of the process, as above described, allows to carry out the process according to the invention under mild conditions, so that no undesired decomposition of the reagents occurs. Additionally, a very high conversion of the alcohol as well as a remarkable selectivity in the formation of the desired perfluorinated fluoroformate are obtained. Furthermore, to achieve full fluorination of all C—H bonds, a large excess of fluorine is not required, conversion of this latter being very high in present process. Without intending to limit the invention to a particular theory, it is believed that the (per)haloolefin acts as radical initiator in the reaction of fluorine specifically with the fluoroformates and thus enables to achieve outstanding reaction rates in the fluorination step.

According to an embodiment of the invention, said at least partially hydrogenated alcohol complies with formula $R_1R_2CHOH$, wherein $R_1$ and $R_2$, independently of each other, are selected in the group consisting of: H, straight-chain, branched-chain and cyclic (oxy)hydrocarbon group, straight-chain, branched-chain and cyclic fluoro(oxy)hydrocarbon group.

In the present specification and in the claims, the term "(oxy)hydrocarbon group" is intended to indicate a hydrocarbon group or an oxyhydrocarbon group comprising one or more than one catenary oxygen atoms. Similarly, the term "fluoro(oxy)hydrocarbon group" is intended to indicate a fluorohydrocarbon group or a fluorooxyhydrocarbon group comprising one or more than one catenary oxygen atoms. Other halogens, e.g. chlorine, might be possibly present in the at least partially hydrogenated alcohol of the invention.

The expression "(per)haloolefin comprising at least one carbon-carbon double bond and having at least one fluorine or chlorine atom on either one of the carbon atoms of said double bond" is intended to encompass fluoroolefins, chloroolefins, and fluorochloroolefins, these compounds possibly comprising one or more heteroatom different from Cl and F, in particular oxygen.

Preferably, said $R_1$ and $R_2$ groups, equal to or different from each other, are independently selected in the group consisting of H, $C_1$-$C_{20}$ (oxy)hydrocarbon group, $C_1$-$C_{20}$ fluoro(oxy)hydrocarbon group, $C_3$-$C_{20}$ cyclo(oxy)hydrocarbon group and $C_3$-$C_{20}$ fluorocyclo(oxy)hydrocarbon group.

According to one embodiment of the process, at least one of said $R_1$ and $R_2$ groups is H, so that said at least partially hydrogenated alcohol is a primary alcohol.

According to another embodiment, said alcohol is obtained in an optional, preliminary step of the process by ionic or radical addition of a hydrogenated alcohol to a perfluorinated or fluorinated olefin.

Said at least partially hydrogenated alcohol may be for example a $C_1$-$C_{18}$ monohydric or dihydric alcohol, preferably a $C_1$-$C_8$ aliphatic alcohol such as methanol, ethanol, 1-propanol, 1-butanol, 1,2-ethanediol, 1,3-propanediol.

The reactions and radical initiators that may be used to synthesize said at least partially hydrogenated, primary or secondary alcohol depend upon the specific desired compounds.

Non limiting examples of suitable perfluorinated or fluorinated olefins that may be used in said ionic or radical addition reaction are notably: $C_2$-$C_{18}$ fluoro and/or perfluoroolefins, such as tetrafluoroethylene (TFE), hexafluoropropylene (HFP), pentafluoropropylene, octafluorobutene, hexafluorobutadiene; perfluoroalkylvinyl ethers, such as perfluoromethylvinylether, perfluoroethylvinylether, perfluoropropylvinylether; and fluorodioxoles, such as perfluorodioxole or perfluoromethoxydioxole.

Thus, in step A of the process, said at least partially hydrogenated alcohol is converted into an at least partially hydrogenated fluoroformate compound.

Standard methods for converting said at least partially hydrogenated alcohol into said fluoroformate can be used. Among others, suitable methods are notably described in GB 1216639 (BAYER AG) Dec. 23, 1970, WO 00/59859 (ISOCHEM SA) Oct. 12, 2000, FLOSSER, D. A., et al. A useful conversion of alcohol to alkyl fluorides. *Tetrahedron lett.* 2002, vol. 43, no. 23, p. 4275-4279., OLAH, G. A., et al. Notes—Synthesis and Investigation of Organic Fluorine Compounds. XVV. The preparation of Alkyl Fluoroformates and Remarks Relative to a New Published Preparation of Alkyl Fluorides. *Journal of Organic Chemistry.* 1956, vol. 21, no. 11, p. 1319-1320.

According to an embodiment of the process, said conversion may be achieved by reacting the alcohol with a reagent selected in the group consisting of carbonyl fluoride, carbonyl fluoride bromide and carbonyl fluoride chloride.

When the alcohol is represented by the formula $R_1R_2CHOH$ (I), wherein $R_1$ and $R_2$ have the above defined meanings, the reaction can be schematized as follows:

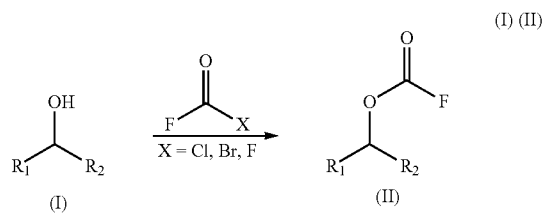

(I) (II)

In case carbonyl fluoride is used, this reagent may be obtained by feeding fluorine, optionally mixed with an inert gas, and carbon monoxide to a reactor in the gas phase and continuously feeding the so obtained carbonyl fluoride to a further reaction vessel containing said alcohol (I). In this case, the molar ratio of carbon monoxide to fluorine ($CO/F_2$) is preferably not less than 1.0, to allow fluorine to fully react with carbon monoxide.

In step A of the process, the at least partially hydrogenated alcohol can be used pure, provided that it is liquid in the reaction conditions, or in a suitable diluent. Among suitable diluents, mention can be notably made of organic halogenated compounds, such as methylene chloride, $CF_3OCFClCF_2Cl$, perfluoropolyethers or hydrogen-containing fluoropolyethers (e.g. those commercialized under trade name GALDEN® PFPE or H-GALDEN® PFPE by Solvay Solexis S.p.A.), fluorinated or perfluorinated ethers (e.g. those commercialized under trade name NOVEC® fluids and HFE® ethers from 3M).

In step B of the process, the fluoroformate compound resulting from step A is reacted with fluorine in the presence of a (per)haloolefin, as above defined, to obtain a perfluorinated fluoroformate compound.

According to one embodiment, the reaction can be schematized as follows:

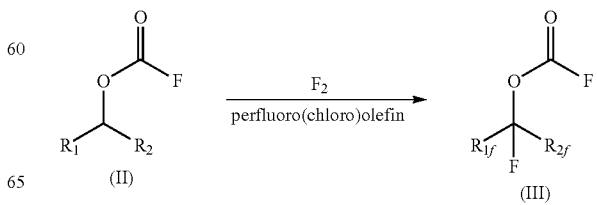

wherein $R_1$, $R_2$ are as above defined, $R_{1f}$ is the perfluorinated equivalent of $R_1$ and $R_{2f}$ is the perfluorinated equivalent of $R_2$. It is understood that if $R_1$ and/or $R_2$ is H, $R_{1f}$ and/or $R_{2f}$ is F; if $R_1$ or $R_2$ is perfluorinated, then $R_1=R_{1f}$ or $R_2=R_{2f}$, respectively.

According to an embodiment of the process, (per)haloolefins suitable for use in step B are those represented by the following formula:

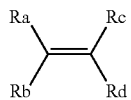

wherein $R_a$, $R_b$, $R_c$ and $R_d$ are each independently selected from the group consisting of F, Cl and hydrocarbon groups, possibly comprising one or more chlorine and/or fluorine atoms, optionally having one or more heteroatoms different from F and Cl, e.g. oxygen, possibly directly linked to the double bond. At least one of $R_a$, $R_b$, $R_c$ and $R_d$ is selected from fluorine or chlorine.

Preferably, $R_a$, $R_b$, $R_c$ and $R_d$ are each independently selected in the group consisting of F, Cl, $C_1$-$C_4$ perfluorocarbon groups, $C_1$-$C_4$ oxygen-containing perfluorocarbon groups, $C_1$-$C_4$ fluorochlorohydrocarbon groups, and $C_1$-$C_4$ oxygen-containing fluorochlorohydrocarbon groups. More preferably, at least three of $R_a$, $R_b$, $R_c$ and $R_d$ are selected from F, Cl and mixtures thereof.

As examples of such (per)haloolefins, mention may be made of tetrafluoroethylene (TFE), hexafluoropropylene (HFP) and its dimers and trimers, octafluorobutene, perfluoropentene, perfluorohexene, perfluoroheptene, perfluorooctene, perfluorocyclobutene, perfluorocyclopentene, perfluorocyclohexene, chlorotrifluoroethylene, dichlorodifluoroethylene, chloropentafluoropropene, perfluorobutadiene, perfluoromethylvinylether, perfluoroethylvinylether, perfluoropropylvinylether; $CF_3OCCl=CClF$, trichloroethylene, tetrachloroethylene, dichloroethylene isomers; and fluorodioxoles of formula:

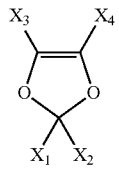

wherein $X_1$, $X_2$, $X_3$, and $X_4$, equal to or different from each other, are independently selected from F, $R_f$ and $OR_f$, wherein $R_f$ is a (per)fluorocarbon group, and wherein at least one of $X_3$ and $X_4$ is fluorine.

The amount of (per)haloolefin used in step B of the process is not critical. According to one embodiment, the amount of said (per)haloolefin is comprised in the range of 0.1 to 50% moles with respect to the hydrogen atoms contained in the fluoroformate compound. Preferably, said amount is comprised in the range of 1% to 30% moles with respect to the hydrogen atoms contained in the fluoroformate compound.

The (per)haloolefin can be initially loaded in the reaction vessel or can be advantageously continuously fed in the required amount during fluorination reaction.

Fluorine may be fed into the reactor as a pure gas or diluted with an inert gas, such as $N_2$, Ar and He.

A hydrogen fluoride scavenger may be used (e.g. NaF, KF).

The fluoroformate compound may be allowed to react with fluorine in a non-solvent phase, provided that it is liquid in the reaction conditions, as well as diluted in a suitable solvent.

Surprisingly, the use of concentrated or pure reagents in step B of the process does not lead to decomposition of the reagents, as the reaction exothermicity may be controlled.

As a matter of fact, the reaction temperature may be advantageously maintained in the range of $-100°$ C. to $+50°$ C.

Typically, fluorine and the (per)haloolefin, in separate feed, are continuously added to the formate at the given temperature or the process. Generally fluorine is added to the reaction in an amount slightly higher than the stoichiometric amount necessary to convert all the hydrogen atoms in the formate to fluorine atoms. Typically, the amount of fluorine is roughly 20% moles, preferably 10% moles higher than said stoichiometric amount. Advantageously, no temperature increase is required to perform the complete fluorination of the formate.

The end of the reaction can be advantageously detected by online analysis, by checking fluorine conversion, which typically suddenly drops to zero.

According to a further embodiment of the process, a further step is comprised, namely:

C. cleaving said perfluorinated fluoroformate compound.

The skilled person will readily understand that, if a primary alcohol is used as the starting at least partially hydrogenated alcohol then cleaving step C leads to a perfluorinated acyl fluoride; under the same conditions, if a secondary alcohol is used as the starting at least partially hydrogenated alcohol then cleaving step C yields a perfluorinated ketone.

According to an embodiment of the process, step C may be schematized as follows:

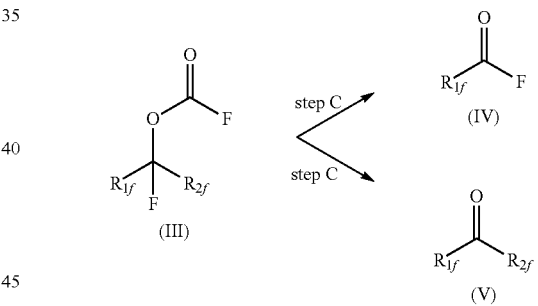

wherein $R_{1f}$ and $R_{2f}$ have the meanings given above. As above mentioned, although the same reaction conditions of step C are applied, a perfluorinated acyl fluoride (IV) results as product of this step if at least one of groups $R_{1f}$ or $R_{2f}$ is F. For illustration purpose only, in the above scheme the situation where $R_{2f}$ is F is shown. In case that both groups $R_{1f}$ or $R_{2f}$ are other than F, step C yields a ketone (V).

Any suitable cleaving or decomposition method or reaction may be used in step C of the process. Said cleaving reaction may be accomplished by thermolysis in the presence of metal fluorides, such as NaF, $CaF_2$, $BaF_2$, AgF, CsF, KF. The temperature for the thermolysis reaction of step C may be comprised in the range of $-70°$ C. to $220°$ C.; preferably, the temperature may be comprised in the range of $-30°$ C. to $150°$ C.

According to a further embodiment of the process, the perfluorinated acyl fluoride (IV) that results from step C may be further subjected to hydrolysis and neutralization in an optional step D of the process, to obtain a perfluorinated carboxylate (VI) as shown in the following scheme:

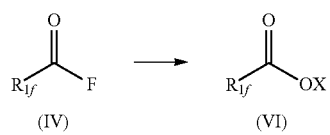

wherein $R_{1f}$ has the same meaning as above defined, and X is H, a monovalent metal or an ammonium group of formula $NR^N_4$, with each $R^N$, independently from each other, is selected from the group consisting of H or a $C_{1-6}$ hydrocarbon group. Step D of the process may be carried out by any conventional hydrolysis and neutralization method which are known to those skilled in the art.

Should the disclosure of any patents, patent applications, and publications which are incorporated herein by reference conflict with the description of the present application to the extent that it may render a term unclear, the present description shall take precedence.

The invention will be now described in more detail with reference to the following examples, whose purpose is merely illustrative and not intended to limit the scope of the invention.

EXAMPLE 1

Conversion of Alcohol (IA) in Fluoroformate (IIA)

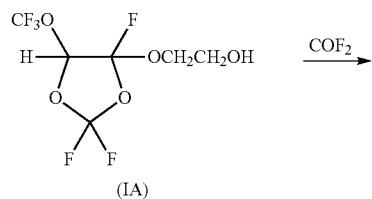

In a 500 ml stainless steel reactor equipped with mechanic stirrer, gas inlet, gas outlet, a thermocouple to check the internal temperature, and external cooling bath, 393 g of an alcohol of the above formula (IA) and 92 g of powdered NaF were introduced and the external temperature set at 15° C.

Then, $COF_2$ (6.0 Nl/h obtained by reaction between 7.0 Nl/h of CO and 6.0 Nl/h of $F_2$) diluted with 2.0 Nl/h of He were introduced into the reactor while keeping reaction medium under vigorous stirring. The off-gases were analysed by a G.C. system to evaluate $COF_2$ conversion. After 6.75 hours feeding was stopped and crude mixture was filtered to separate inorganic salts. The liquid product was analyzed by $^{19}F$ NMR showing an almost quantitative conversion of the starting alcohol and selectivity in the desired fluoroformate.

EXAMPLE 2

Fluorination of Fluoroformate (IIA)

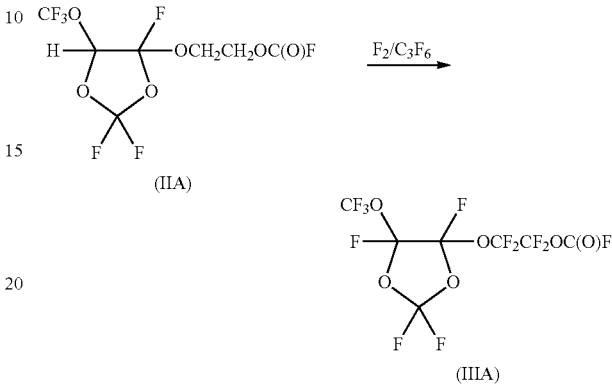

In a 500 ml stainless steel reactor equipped with mechanic stirrer, two gas inlets, one gas outlet, a thermocouple to check the internal temperature, and external cooling bath, 278 g of a fluoroformate of the above formula (IIA) were loaded and the external temperature set at 0° C.

Then, two different stream of gases were introduced by the inlets into the reactor kept under vigorous stirring: $F_2$ (2.3 Nl/h) diluted with 4.5 Nl/h of He, and $C_3F_6$ (0.3 Nl/h) diluted with 1.5 Nl/h of He. The off-gases went through a NaF trap and analyzed by GC to evaluate $F_2$ conversion and thus estimate the C—H to C—F conversion. The internal temperature remained constant at +5° C. After 57 hours, the internal temperature fell quickly from 5° C. to 0° C., and no additional $F_2$ conversion was observed. The feeding was stopped and the residual HF was removed by inert gas. The crude mixture was collected and analyzed by GC and $^{19}F$ NMR. The desired perfluorofluoroformate (IIIA) was obtained with 95% yield.

EXAMPLE 3

Conversion of Alcohol (IB) in Fluoroformate (IIB)

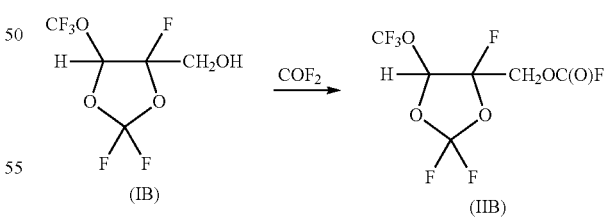

In a 250 ml stainless steel reactor equipped with mechanic stirrer, gas inlet, gas outlet, a thermocouple to check the internal temperature, and external cooling bath, 99 g of a alcohol of the above formula (IB) and 34 g of powdered NaF were loaded and the external temperature set at 15° C. Then, $COF_2$ (2.0 Nl/h obtained by reaction between 2.5 Nl/h of CO and 2.0 Nl/h of $F_2$) diluted with 1.0 Nl/h of He were introduced into the reactor kept under vigorous stirring. The off-gases were analysed by a GC system to evaluate $COF_2$ conversion. After 6.0 hours feeding was stopped and crude mixture was filtered to separate inorganic salts. The liquid product was analyzed by $^{19}F$ NMR showing an almost quantitative conversion of the starting alcohol and selectivity in the desired fluoroformate.

EXAMPLE 4

Fluorination of Fluoroformate (IIB)

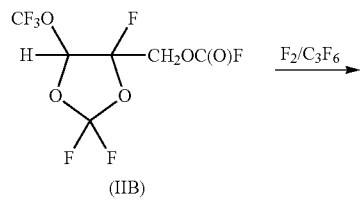

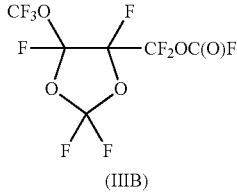

In a 250 ml stainless steel reactor equipped with mechanic stirrer, two gas inlets, one gas outlet, a thermocouple to check the internal temperature, and external cooling bath, 81 g of the fluoroformate of formula (IIB) were introduced and fluorinated according to the same procedure of Example 1, with the exception that $F_2$ was fed at 1.8 Nl/h, diluted with 3.0 Nl/h of He. After 15 hours, the internal temperature fell quickly from 5° C. to 0° C., and no additional $F_2$ conversion was observed. The crude mixture was collected and analyzed by GC and $^{19}F$ NMR. The desired perfluorofluoroformate (IIIB) was obtained with 96% yield.

COMPARATIVE EXAMPLE 5

Fluorination of Fluoroformate (IIA) in the Absence of Haloolefin

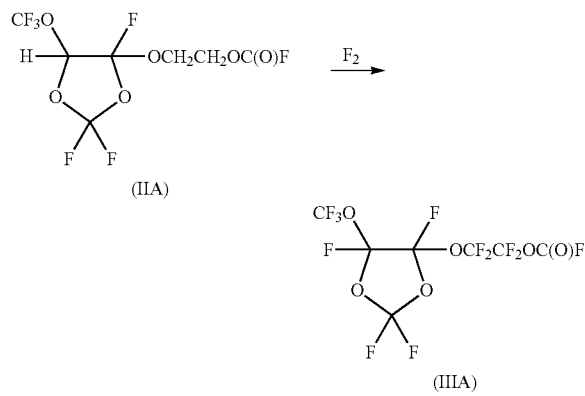

In a 100 ml stainless steel reactor equipped with mechanic stirrer, gas inlet, gas outlet, a thermocouple to check the internal temperature, and external cooling bath, 60 g of a fluoroformate of the above formula (IIA) were introduced and the external temperature set at 0° C.

Then, $F_2$ (1.5 Nl/h) diluted with 4.5 Nl/h of He was introduced by the inlet into the reactor kept under vigorous stirring. The off-gases went through a NaF trap and were analyzed by GC to evaluate $F_2$ conversion. The internal temperature slowly decreased from +5° C. (at the beginning) to 0° C. in 22 hours and the same did the fluorine conversion. The feeding was stopped and the residual HF was removed by inert gas. The crude mixture was collected and analyzed by $^{19}F$ NMR: a complex mixture of partially fluorinated formates was formed. The conversion of C—H to C—F was 66%, despite the excess of fluorine fed.

EXAMPLE 6

Decomposition of Perfluoroformate (IIIA) into Acyl Fluoride

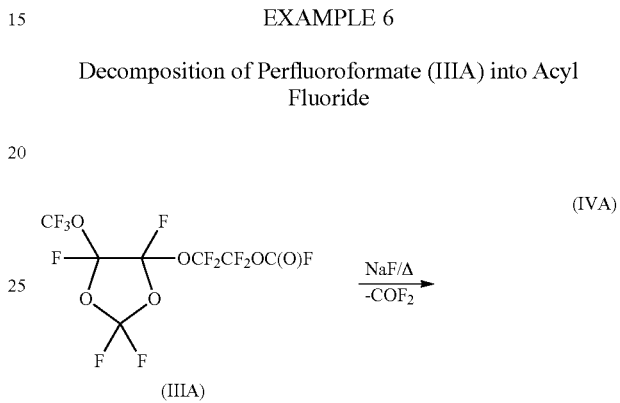

In a 250 ml stainless steel reactor containing 5 g of anhydrous NaF, 50 g of the perfluoroformate (IIIA) were introduced; the reactor was then heated at 50° C. and maintained under stirring for 24 hours. The $COF_2$ produced by the reaction was evacuated at 20° C. and the acyl fluoride was recovered by filtration. The conversion of the starting formate and the selectivity to the acyl fluoride were quantitative.

Possible modifications and/or additions may be made by those skilled in the art to the hereinabove disclosed and illustrated embodiment while remaining within the scope of the following claims.

The invention claimed is:
1. A process for producing a perfluorinated functional compound, which comprises:
   Step A. converting an at least partially hydrogenated alcohol into corresponding at least partially hydrogenated fluoroformate compound;
   Step B. reacting said at least partially hydrogenated fluoroformate compound with fluorine in the presence of at least one (per)haloolefin comprising at least one carbon-carbon double bond and having at least one fluorine or chlorine atom on either of carbon atoms of said double bond, to obtain a perfluorinated fluoroformate compound.
2. The process according to claim 1, wherein said at least partially hydrogenated alcohol complies with formula $R_1R_2CHOH$, wherein $R_1$ and $R_2$, independently of each other, are selected from the group consisting of H, straight-chain, branched-chain or cyclic (oxy)hydrocarbon group, and straight-chain, branched-chain or cyclic fluoro(oxy)hydrocarbon.

3. The process according to claim 2, wherein $R_1$ and $R_2$ equal to or different from each other, are independently selected from the group consisting of H, $C_1$-$C_{20}$ (oxy)hydrocarbon group, $C_1$-$C_{20}$ fluoro(oxy)hydrocarbon group, $C_3$-$C_{20}$ cyclo(oxy)hydrocarbon group and $C_3$-$C_{20}$ fluorocyclo(oxy)hydrocarbon group.

4. The process according to claim 1, wherein in said step A said at least partially hydrogenated alcohol is reacted with a reagent selected from the group consisting of carbonyl fluoride, carbonyl fluoride bromide and carbonyl fluoride chloride.

5. The process according to claim 1, wherein in said step A said at least partially hydrogenated alcohol is reacted with carbonyl fluoride.

6. The process according to claim 1, wherein in said step B said (per)haloolefin complies with the following formula:

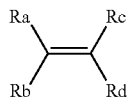

wherein $R_a$, $R_b$, $R_c$ and $R_d$ are each independently selected from the group consisting of F, Cl and hydrocarbon groups.

7. The process according to claim 6, wherein $R_a$, $R_b$, $R_c$ and $R_d$ are each independently selected from the group consisting of F, Cl, $C_1$-$C_4$ perfluorocarbon groups, $C_1$-$C_4$ oxygen-containing perfluorocarbon groups, $C_1$-$C_4$ fluorochlorohydrocarbon groups, and $C_1$-$C_4$ oxygen-containing fluorochlorohydrocarbon groups.

8. The process according to claim 7, wherein in said step B said (per)haloolefin is selected from the group consisting of tetrafluoroethylene (TFE), hexafluoropropylene (HFP) and its dimers and trimers, octafluorobutene, perfluoropentene, perfluorohexene, perfluoroheptene, perfluorooctene, perfluorocyclobutene, perfluorocyclopentene, perfluorocyclohexene, chlorotrifluoroethylene, dichlorodifluoroethylene, chloropentafluoropropene, perfluorobutadiene, perfluoromethylvinylether, perfluoroethylvinylether, perfluoropropylvinylether; $CF_3OCCl=CClF$, trichloroethylene, tetrachloroethylene, dichloroethylene isomers; and fluorodioxoles of formula:

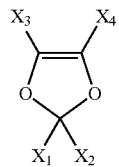

wherein $X_1$, $X_2$, $X_3$, and $X_4$, equal to or different from each other, are independently selected from the group consisting of F, $R_f$ and $OR_f$, wherein $R_f$ is a (per)fluorocarbon group.

9. The process according to claim 1, wherein in said step B the amount of said (per)haloolefin is in the range of 1 to 20% moles with respect to said at least partially hydrogenated fluoroformate.

10. The process according to claim 1, comprising cleaving said perfluorinated fluoroformate compound.

11. The process according to claim 1, wherein cleaving of said perfluorinated fluoroformate compound is achieved by thermolysis in the presence of a metal fluoride.

* * * * *